(12) United States Patent
Sugihara

(10) Patent No.: US 10,184,886 B2
(45) Date of Patent: Jan. 22, 2019

(54) ATOMIC ABSORPTION PHOTOMETER AND ATOMIC ABSORPTION MEASUREMENT METHOD

(71) Applicant: SHIMADZU CORPORATION, Kyoto-shi, Kyoto (JP)

(72) Inventor: Kazuo Sugihara, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 0 days.

(21) Appl. No.: 15/525,327

(22) PCT Filed: Nov. 11, 2014

(86) PCT No.: PCT/JP2014/079808
§ 371 (c)(1),
(2) Date: May 9, 2017

(87) PCT Pub. No.: WO2016/075751
PCT Pub. Date: May 19, 2016

(65) Prior Publication Data
US 2017/0322147 A1 Nov. 9, 2017

(51) Int. Cl.
*G01J 3/36* (2006.01)
*G01N 21/31* (2006.01)
*G01J 3/10* (2006.01)
*G01J 3/42* (2006.01)

(52) U.S. Cl.
CPC ............ *G01N 21/3103* (2013.01); *G01J 3/10* (2013.01); *G01J 3/42* (2013.01); *G01N 2021/3111* (2013.01)

(58) Field of Classification Search
CPC .. G01N 21/3103; G01N 21/274; G01N 21/71; G01N 2021/3111; G01N 2021/3118; G01J 3/10; G01J 3/42443; G01J 2003/106; G01J 2003/4334; G01J 2003/4336; G01J 2003/323
USPC ......................................... 356/307, 315, 316
See application file for complete search history.

(56) References Cited

U.S. PATENT DOCUMENTS

| | | | | |
|---|---|---|---|---|
| 4,989,975 A * | 2/1991 | Dencks | .............. | G01N 21/3103 356/307 |
| 5,042,946 A * | 8/1991 | Harada | .............. | G01N 21/3103 356/307 |
| 2002/0080351 A1 | 6/2002 | Sakai | | |

FOREIGN PATENT DOCUMENTS

JP  2002-195946 A  7/2002

* cited by examiner

*Primary Examiner* — Tarifur R Chowdhury
*Assistant Examiner* — Jonathon Cook
(74) *Attorney, Agent, or Firm* — Sughrue Mion, PLLC

(57) ABSTRACT

There are provided an atomic absorption photometer and an atomic absorption measurement method which can easily perform background correction in a short time period by using a plurality of types of methods while suppressing the amount of samples consumed. Background correction is performing by using each of the D2 lamp method, the Zeeman method, and a self-reversal method, according to measurement data in each of measurement periods T41 to T46 obtained in one data acquisition cycle. Background correction is performed on the common measurement data (atomic absorption data) obtained in the atomic absorption measurement period T41, by using the measurement data (background data) obtained in each of the first to third background measurement periods T44, T46, and T42.

7 Claims, 10 Drawing Sheets

ATOMIC ABSORPTION PHOTOMETER AND ATOMIC ABSORPTION MEASUREMENT METHOD

CROSS REFERENCE TO RELATED APPLICATIONS

This application is a National Stage of International Application No. PCT/JP2014/079808 filed Nov. 11, 2014, the contents of which are incorporated herein by reference in its entirety.

TECHNICAL FIELD

The present invention relates to an atomic absorption photometer and an atomic absorption measurement method for measuring atomic absorption by atomizing a sample and generating atomic vapor, and then irradiating the atomic vapor with a measuring beam.

BACKGROUND ART

An atomic absorption photometer includes an atomization unit which atomizes a sample. At the atomization unit, atomic vapor is generated due to atomization of a sample, and the atomic vapor is irradiated with a measuring beam from a light source. A light source which emits a bright line spectrum, such as a hollow cathode lamp (HCL), is used as the above light source. In a case where atomic vapor is irradiated with a measuring beam from such a light source, since light of a specific wavelength is absorbed in the atomic vapor, the sample can be analyzed by measuring absorbance of the light.

In an analysis of a sample using the atomic absorption photometer, for example, in a case where a large amount of mixtures such as salts are mixed in the sample, the mixtures may not dissociate completely even at high temperature, and a measuring beam from the light source may be absorbed by the mixture. As described, absorption may occur due to a factor other than absorption by a target element, and such absorption is referred to as background absorption (for example, see Patent Document 1 listed below).

In a case where background absorption occurs, since absorbance due to background absorption is added to absorbance due to atomic absorption of a target element, it is difficult to accurately measure absorbance due to atomic absorption. Therefore, in order to eliminate the influence of background absorption, background correction is performed by using the D2 lamp method, the Zeeman method, a self-reversal method (SR method), or the like.

In the D2 lamp method, background correction is performed, by irradiating atomic vapor generated at the atomization unit with a measuring beam for background measurement by using, for example, a D2 lamp (deuterium lamp). That is, in a case where background correction is performed by using the D2 lamp method, a light source which emits a continuous spectrum is used in addition to a light source which emits, for example, a bright line spectrum, calculation is performed by using spectra obtained by irradiating atomic vapor with measuring beams from the light sources, and thus background correction is performed.

In the Zeeman method, background correction is performed, by generating a magnetic field at the atomization unit from a magnetic field generation unit such as an electromagnet. That is, in a case where background correction is performed by using the Zeeman method, operation of the magnetic field generation unit is switched when atomic vapor is irradiated with a measuring beam from the light source which emits, for example, a bright line spectrum, calculation is performed by using the spectrum obtained at that time, and thus background correction is performed.

In the self-reversal method, background correction is performed by irradiating atomic vapor generated at the atomization unit with a measuring beam, for example, with an overcurrent. That is, in a case where background correction is performed by using the self-reversal method, a measuring beam is emitted for a fixed short time period with an overcurrent when atomic vapor is irradiated with the measuring beam from the light source which emits, for example, a bright line spectrum, calculation is performed by using the spectrum obtained at that time, and thus background correction is performed.

PRIOR ART DOCUMENT

Patent Document

Patent Document 1: JP 2002-195946 A

SUMMARY OF THE INVENTION

Problems to be Solved by the Invention

Each of the above-described methods for back ground correction has unique advantages and disadvantages. Therefore, even if analyses are conducted on an identical sample, measurement results may differ from one another or measurement conditions may differ from one another among the methods.

For example, when background correction is performed by using the D2 lamp method, in a case where there is an absorption line of another element with a wavelength extremely close to the wavelength of an absorption line of a target element, the absorption line of the other element may not be determined as background and background correction may be inaccurate. From such a viewpoint, background correction can be performed more accurately by using the Zeeman method or the self-reversal method. However, the D2 lamp method may be preferable if sensitivity (S/N ratio) and accuracy of correction are taken into consideration. In contrast, the Zeeman method is advantageous in that a measurable wavelength range is wide. In addition, background correction is preferably performed by using the self-reversal method in order to reduce power consumption.

As described, since the measurement result, the measurement condition, and another operation manner vary depending on the method for performing background correction, a sample needs to be analyzed by selecting an optimal method. Therefore, an operator conventionally performs background correction by using each of the above various methods, compares and examines the measurement results and the like, and thus selects the optimal method. However, there is a problem that work of repeatedly performing background correction by using a plurality of types of methods is troublesome, takes time, and consumes a large amount of samples.

The present invention is made in view of the above circumstances, and an object of the present invention is to provide an atomic absorption photometer and an atomic absorption measurement method which can easily perform background correction in a short time period by using a plurality of types of methods while suppressing the amount of samples consumed.

Means for Solving the Problems

An atomic absorption photometer according to the present invention includes an atomization unit, a first light source, a second light source, a magnetic field generation unit, a detector, a measurement data acquisition processing unit, a first background correction processing unit, a second background correction processing unit, and a third background correction processing unit. The atomization unit generates atomic vapor by atomizing a sample. The first light source irradiates the atomic vapor generated at the atomization unit with a measuring beam for atomic absorption measurement. The second light source irradiates the atomic vapor generated at the atomization unit with a measuring beam for background measurement. The magnetic field generation unit generates a magnetic field at the atomization unit. The detector acquires measurement data by detecting light having passed through the atomization unit.

The measurement data acquisition processing unit acquires measurement data in each of an atomic absorption measurement period, a first background measurement period, a second background measurement period, and a third background measurement period, in a data acquisition cycle including the above measurement periods. In the atomic absorption measurement period, a measuring beam is emitted from the first light source in a state where no magnetic field is generated by the magnetic field generation unit. In the first background measurement period, a measuring beam is emitted from the second light source in a state where no magnetic field is generated by the magnetic field generation unit. In the second background measurement period, a measuring beam is emitted from the first light source in a state where a magnetic field is generated by the magnetic field generation unit. In the third background measurement period, a measuring beam is emitted from the first light source with an overcurrent in a state where no magnetic field is generated by the magnetic field generation unit.

The first background correction processing unit corrects the measurement data obtained in the atomic absorption measurement period by using the D2 lamp method, according to the measurement data obtained in the first background measurement period. The second background correction processing unit corrects the measurement data obtained in the atomic absorption measurement period by using the Zeeman method, according to the measurement data obtained in the second background measurement period. The third background correction processing unit corrects the measurement data obtained in the atomic absorption measurement period by using a self-reversal method, according to the measurement data obtained in the third background measurement period.

According to such a configuration, background correction is performed by using each of the D2 lamp method, the Zeeman method, and the self-reversal method, according to the measurement data in each measurement period obtained in one data acquisition cycle. That is, background correction is performed on the common measurement data (atomic absorption data) obtained in the atomic absorption measurement period, by using the measurement data (background data) obtained in each of the first to third background measurement periods. Therefore, according to such a configuration, background correction can be more easily performed in a shorter time period by using a plurality of types of methods while suppressing the amount of samples consumed than in a configuration where atomic absorption data and background data are acquired in each of the plurality of types of methods.

The measurement data acquisition processing unit may acquire measurement data in each of the atomic absorption measurement period, the first background measurement period, and the second background measurement period, in a data acquisition cycle including only the above measurement periods. In this case, the atomic absorption photometer may not include the third background correction processing unit.

According to such a configuration, background correction is performed by using each of the D2 lamp method and the Zeeman method, according to the measurement data in each measurement period obtained in one data acquisition cycle. That is, background correction is performed on the common measurement data (atomic absorption data) obtained in the atomic absorption measurement period, by using the measurement data (background data) obtained in each of the first and second background measurement periods. Therefore, according to such a configuration, background correction can be more easily performed in a shorter time period by using a plurality of types of methods while suppressing the amount of samples consumed than in a configuration where atomic absorption data and background data are acquired in each of the plurality of types of methods.

The measurement data acquisition processing unit may acquire measurement data in each of the atomic absorption measurement period, the second background measurement period, and the third background measurement period, in a data acquisition cycle including only the above measurement periods. In this case, the atomic absorption photometer may not include the first background correction processing unit.

According to such a configuration, background correction is performed by using each of the Zeeman method and the self-reversal method, according to the measurement data in each measurement period obtained in one data acquisition cycle. That is, background correction is performed on the common measurement data (atomic absorption data) obtained in the atomic absorption measurement period, by using the measurement data (background data) obtained in each of the second and third background measurement periods. Therefore, according to such a configuration, background correction can be more easily performed in a shorter time period by using a plurality of types of methods while suppressing the amount of samples consumed than in a configuration where atomic absorption data and background data are acquired in each of the plurality of types of methods.

The measurement data acquisition processing unit may acquire measurement data in each of the atomic absorption measurement period, the first background measurement period, and the third background measurement period, in a data acquisition cycle including only the above measurement periods. In this case, the atomic absorption photometer may not include the second background correction processing unit.

According to such a configuration, background correction is performed by using each of the D2 lamp method and the self-reversal method, according to the measurement data in each measurement period obtained in one data acquisition cycle. That is, background correction is performed on the common measurement data (atomic absorption data) obtained in the atomic absorption measurement period, by using the measurement data (background data) obtained in each of the first and third background measurement periods. Therefore, according to such a configuration, background correction can be more easily performed in a shorter time period by using a plurality of types of methods while suppressing the amount of samples consumed than in a configuration where atomic absorption data and background data are acquired in each of the plurality of types of methods.

An atomic absorption measurement method according to the present invention is an atomic absorption measurement method for measuring atomic absorption by using an atomic absorption photometer including an atomization unit which generates atomic vapor by atomizing a sample, a first light source which irradiates the atomic vapor generated at the atomization unit with a measuring beam for atomic absorption measurement, a second light source which irradiates the atomic vapor generated at the atomization unit with a measuring beam for background measurement, a magnetic field generation unit which generates a magnetic field at the atomization unit, and a detector which acquires measurement data by detecting light having passed through the atomization unit. The atomic absorption measurement method includes a measurement data acquisition step, a first background correction step, a second background correction step, and a third background correction step.

In the measurement data acquisition step, measurement data in each of an atomic absorption measurement period, a first background measurement period, a second background measurement period, and a third background measurement period is acquired in a data acquisition cycle including the above measurement periods. In the atomic absorption measurement period, a measuring beam is emitted from the first light source in a state where no magnetic field is generated by the magnetic field generation unit. In the first background measurement period, a measuring beam is emitted from the second light source in a state where no magnetic field is generated by the magnetic field generation unit. In the second background measurement period, a measuring beam is emitted from the first light source in a state where a magnetic field is generated by the magnetic field generation unit. In the third background measurement period, a measuring beam is emitted from the first light source with an overcurrent in a state where no magnetic field is generated by the magnetic field generation unit.

In the first background correction step, measurement data obtained in the atomic absorption measurement period is corrected by using the D2 lamp method, according to the measurement data obtained in the first background measurement period. In the second background correction step, measurement data obtained in the atomic absorption measurement period is corrected by using the Zeeman method, according to the measurement data obtained in the second background measurement period. In the third background correction step, the measurement data obtained in the atomic absorption measurement period is corrected by using a self-reversal method, according to the measurement data obtained in the third background measurement period.

In the measurement data acquisition step, the measurement data in each of the atomic absorption measurement period, the first background measurement period, and the second background measurement period may be acquired in a data acquisition cycle including only the above measurement periods. In this case, the atomic absorption measurement method may not include the third background correction step.

In the measurement data acquisition step, the measurement data in each of the atomic absorption measurement period, the second background measurement period, and the third background measurement period may be acquired in a data acquisition cycle including only the above measurement periods. In this case, the atomic absorption measurement method may not include the first background correction step.

In the measurement data acquisition step, the measurement data in each of the atomic absorption measurement period, the first background measurement period, and the third background measurement period may be acquired in a data acquisition cycle including only the above measurement periods. In this case, the atomic absorption measurement method may not include the second background correction step.

Effects of the Invention

According to the present invention, background correction can be more easily performed in a shorter time period by using a plurality of types of methods while suppressing the amount of samples consumed than in a configuration where atomic absorption data and background data are acquired in each of the plurality of types of methods.

MODE FOR CARRYING OUT THE INVENTION

First Embodiment

Figure 1:
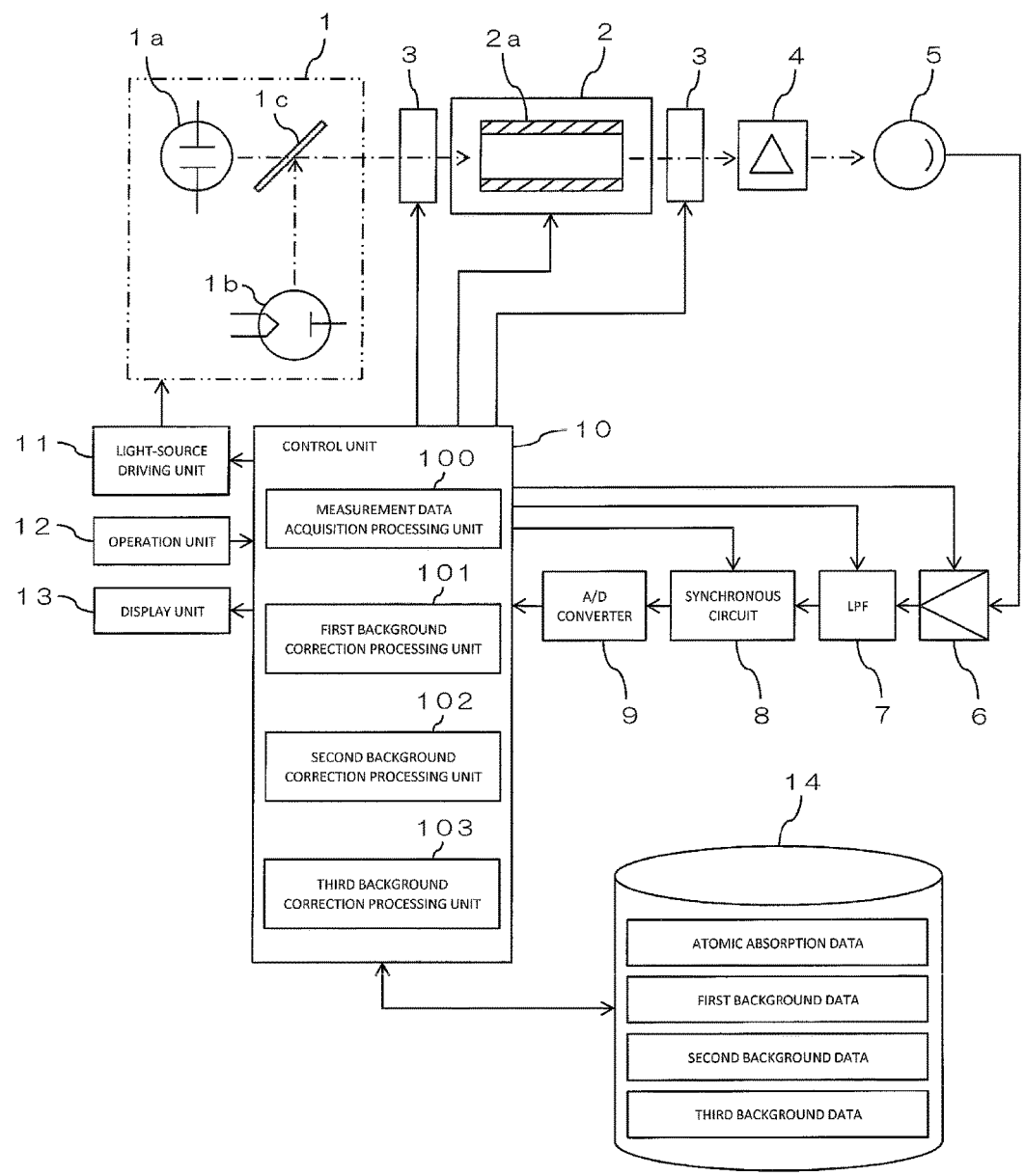
FIG. 1 is a diagram illustrating a configuration example of an atomic absorption photometer according to a first embodiment of the present invention.

FIG. 1 is a diagram illustrating a configuration example of an atomic absorption photometer according to a first embodiment of the present invention. This atomic absorption photometer is a so-called furnace-type atomic absorption photometer, and is configured to generate atomic vapor by heating and atomizing a sample in a graphite tube 2a, to cause a measuring beam to pass through the atomic vapor, and to measure absorbance of the sample.

The atomic absorption photometer includes a light source unit 1, an atomization unit 2, a magnetic field generation unit 3, a spectroscope 4, a photomultiplier tube 5, an amplifier 6, a low-pass filter (LPF) 7, a synchronous circuit 8, an A/D converter 9, a control unit 10, a light-source driving unit 11, an operation unit 12, a display unit 13, a memory 14, and the like.

The light source unit 1 includes a hollow cathode lamp (HCL) 1a, a deuterium lamp (D2L) 1b, and a half mirror 1c. The hollow cathode lamp 1a is a first light source which emits a measuring beam including a bright line spectrum. In contrast, the deuterium lamp 1b is a second light source which emits a measuring beam including a continuous spectrum. The measuring beams emitted from the hollow cathode lamp 1a and the deuterium lamp 1b enter the graphite tube 2a of the atomization unit 2 via the half mirror 1c.

A sample solution is injected into the graphite tube 2a through a sample injection port (not illustrated), and the sample solution is heated by the graphite tube 2a where a high current flows. Thus, the sample is atomized and atomic vapor is generated in the graphite tube 2a. The atomic vapor generated in the graphite tube 2a is irradiated with the measuring beams from the hollow cathode lamp 1a and the deuterium lamp 1b. At that time, light of a wavelength specific to an element included in the sample is strongly absorbed while the measuring beam from the hollow cathode lamp 1a is passing through the atomic vapor in the graphite tube 2a.

Light which has passed through the atomization unit 2 enters the spectroscope 4. The spectroscope 4 includes, for example, a diffraction grating, and light dispersed by the diffraction grating enters the photomultiplier tube 5. The photomultiplier tube 5 is an example of the detector for acquiring measurement data by detecting the light having passed through the atomization unit 2. The photomultiplier tube 5 outputs a signal corresponding to intensity of received light as measurement data.

The control unit 10 causes the hollow cathode lamp 1a and the deuterium lamp 1b to perform pulse lighting by controlling the light-source driving unit 11. The measuring beams from the hollow cathode lamp 1a and the deuterium lamp 1b pass through the atomization unit 2 and the spectroscope 4 and then are detected by the photomultiplier tube 5, and time-division multiplexed (TDM) signals are output from the photomultiplier tube 5.

After the signals output from the photomultiplier tube 5 are amplified by the amplifier 6, high-frequency noise is removed from the signals by the low-pass filter 7. Then, the signals are input to the synchronous circuit 8. In the synchronous circuit 8, the signal which is based on the measuring beam from the hollow cathode lamp 1a and which is output from the photomultiplier tube 5 is separated from the signal which is based on the measuring beam from the deuterium lamp 1b and which is output from the photomultiplier tube 5. The separated output signals are converted into digital signals by the A/D converter 9 and are input to the control unit 10.

The measuring beam from the hollow cathode lamp 1a is a measuring beam for atomic absorption measurement. That is, the signal which is based on the measuring beam from the hollow cathode lamp 1a and which is output from photomultiplier tube 5 is measurement data influenced by absorption (atomic absorption) performed by the target element, and by absorption (background absorption) other than the atomic absorption. In contrast, the measuring beam from the deuterium lamp 1b is a measuring beam for background measurement. The influence of atomic absorption on the signal which is based on the measuring beam from the deuterium lamp 1b and which is output from the photomultiplier tube 5 is small enough to be ignored, and therefore the signal can be considered to be equivalent to measurement data which is influenced only by background absorption.

Therefore, absorbance due to atomic absorption of the target element can be determined by correcting measurement data (atomic absorption data) obtained by emitting a measuring beam from the hollow cathode lamp 1a, according to the measurement data (first background data) obtained by emitting a measuring beam from the deuterium lamp 1b. Such a background correction method is called the D2 lamp method.

In the present embodiment, background correction can also be performed by using another method such as the Zeeman method or a self-reversal method in addition to the above D2 lamp method. The magnetic field generation unit 3 is configured to generate a magnetic field at the atomization unit 2, and is used when background correction is performed by using the Zeeman method. In this example, the magnetic field generation unit 3 is configured of a pair of coils arranged on an optical axis of the measuring beam so as to interpose the graphite tube 2a therebetween. By feeding current to the coils, a magnetic field can be generated in a direction parallel to the optical axis of the measuring beam.

In a case where a measuring beam is emitted from the hollow cathode lamp 1a in a state where no magnetic field is generated by the magnetic field generation unit 3, measurement data influenced by atomic absorption and background absorption is obtained as described above. In contrast, the influence of atomic absorption on measurement data obtained in a case where a measuring beam is emitted from the hollow cathode lamp 1a in a state where a magnetic field is generated by the magnetic field generation unit 3 is small enough to be ignored, and therefore, the measurement data can be considered to be equivalent to the measurement data influenced only by background absorption.

Therefore, in the Zeeman method, absorbance due to atomic absorption of the target element can be determined by correcting the measurement data (atomic absorption data) obtained by emitting a measuring beam from the hollow cathode lamp 1a in the state where no magnetic field is generated by the magnetic field generation unit 3, according to measurement data (second background data) obtained by emitting a measuring beam from the hollow cathode lamp 1a in the state where a magnetic field is generated by the magnetic field generation unit 3.

In the self-reversal method (self-absorption method), measurement data obtained in background measurement is acquired by emitting a measuring beam from the hollow cathode lamp 1a with an overcurrent in a state where no magnetic field is generated by the magnetic field generation unit 3. The influence of atomic absorption on measurement data obtained by emitting a measuring beam from the hollow cathode lamp 1a for a short time period with an overcurrent of about 100 to 600 mA, for example, is small enough to be ignored, and therefore, the measurement data can be considered to be equivalent to the measurement data influenced only by background absorption.

Therefore, in the self-reversal method, absorbance due to atomic absorption of the target element can be determined by correcting the measurement data (atomic absorption data) obtained by emitting a measuring beam from the hollow cathode lamp 1a with a normal current (for example, less than 30 mA), according to measurement data (third background data) obtained by emitting a measuring beam from the hollow cathode lamp 1a with an overcurrent.

The control unit 10 has a configuration including, for example, a CPU (Central Processing Unit), and controls operation of each constituent included in the atomic absorption photometer. The atomization unit 2, the magnetic field generation unit 3, the amplifier 6, the low-pass filter 7, the synchronous circuit 8, the A/D converter 9, the light-source driving unit 11, the operation unit 12, the display unit 13, the memory 14, and the like are electrically connected to the control unit 10.

The operation unit 12 has a configuration including, for example, a keyboard or a mouse, and an operator can perform input operation by operating the operation unit 12. The display unit 13 is configured, for example, of a liquid crystal display, and can display the result of processing performed by the control unit 10 and the like on a display screen. The memory 14 is configured of, for example, a RAM (Random Access Memory) or a hard disk.

The control unit 10 causes the CPU to execute a program and thus functions as a measurement data acquisition processing unit 100, a first background correction processing unit 101, a second background correction processing unit 102, a third background correction processing unit 103, and the like. The measurement data acquisition processing unit 100 performs a process of acquiring the atomic absorption data, the first background data, the second background data, and the third background data described above, as measurement data, and storing the data in the memory 14.

The first background correction processing unit 101 performs background correction by using the D2 lamp method, according to the atomic absorption data and the first background data. The second background correction processing unit 102 performs background correction by using the Zeeman method, according to the atomic absorption data and the second background data. The third background correction processing unit 103 performs background correction by using the self-reversal method, according to the atomic absorption data and the third background data.

Figure 2:
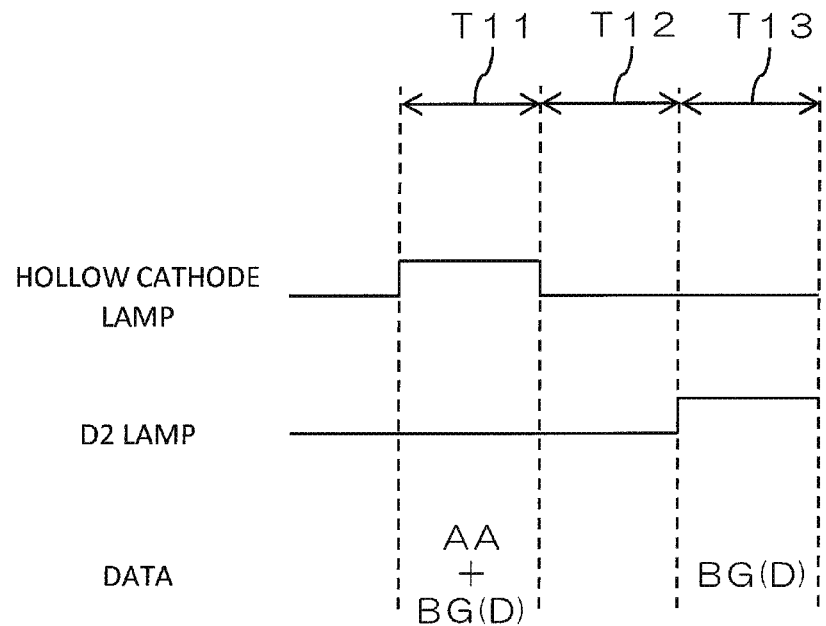
FIG. 2 is a timing chart for explaining a manner of performing background correction by using the D2 lamp method.

FIG. 2 is a timing chart for explaining a manner of performing background correction by using the D2 lamp method. In a case where background correction is performed by using the D2 lamp method, operation of the hollow cathode lamp 1a and operation of the deuterium lamp 1b are controlled in a predetermined manner, and thus the measurement data acquisition processing unit 100 acquires signals output from the photomultiplier tube 5 as measurement data in a fixed data acquisition cycle.

The above data acquisition cycle in background correction performed by using the D2 lamp method includes an atomic absorption measurement period T11 in which a measuring beam is emitted from the hollow cathode lamp 1a in the state where no magnetic field is generated by the magnetic field generation unit 3, a first background measurement period T13 in which a measuring beam is emitted from the deuterium lamp 1b in a state where no magnetic field is generated by the magnetic field generation unit 3, and a dark period T12 provided between the above measurement periods. In the dark period T12, the hollow cathode lamp 1a and the deuterium lamp 1b are brought into an unlit state or a low-output lit state. By performing calculation according to measurement data obtained in each of the periods T11 to T13, background correction using the D2 lamp method can be performed.

Here, the measurement data obtained in the atomic absorption measurement period T11 is measurement data H influenced by atomic absorption (AA) and background absorption (BG(D)). In contrast, the measurement data obtained in the first background measurement period T13 can be considered to be equivalent to measurement data D influenced only by background absorption (BG(D)). Absorbance can be obtained by using the following formula (1), according to the measurement data H and D, and measurement data Δ obtained in the dark period T12. Note that F(X) is a function representing a calculation formula for absorbance calculation on measurement data X.

Figure 3:
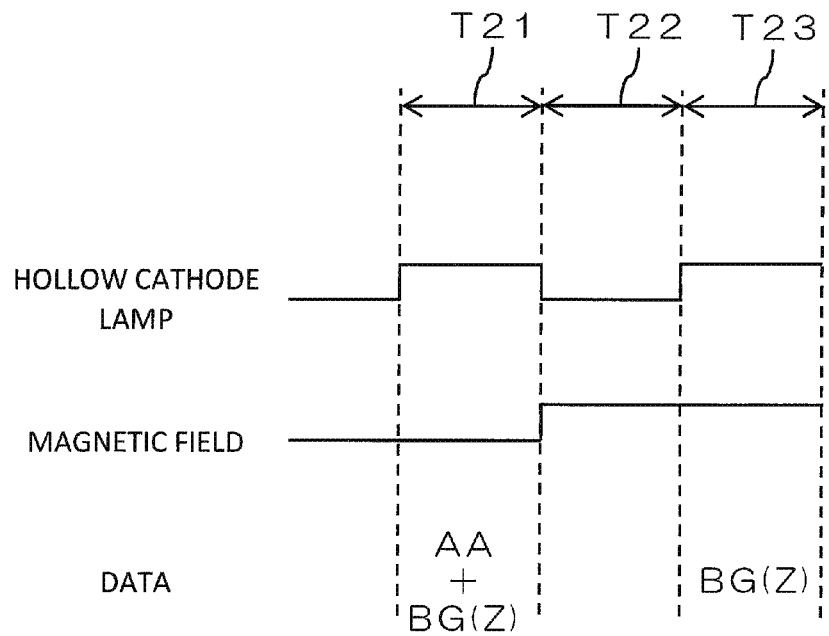
FIG. 3 is a timing chart for explaining a manner of performing background correction by using the Zeeman method.

Absorbance=$F(H-\Delta)-F(D-\Delta)$   Formula (1):

FIG. 3 is a timing chart for explaining a manner of performing background correction by using the Zeeman method. In a case where background correction is performed by using the Zeeman method, operation of the hollow cathode lamp 1a and operation of the magnetic field generation unit 3 are controlled in a predetermined manner, and thus the measurement data acquisition processing unit 100 acquires signals output from the photomultiplier tube 5 as measurement data in a fixed data acquisition cycle.

The above data acquisition cycle in background correction performed by using the Zeeman method includes an atomic absorption measurement period T21 in which a measuring beam is emitted from the hollow cathode lamp 1a in the state where no magnetic field is generated by the magnetic field generation unit 3, a second background measurement period T23 in which a measuring beam is emitted from the hollow cathode lamp 1a in a state where a magnetic field is generated by the magnetic field generation unit 3, and a dark period T22 provided between the above measurement periods. In the dark period T22, the hollow cathode lamp 1a is brought into an unlit state or a low-output lit state. By performing calculation according to measurement data obtained in each of the periods T21 to T23, background correction using the Zeeman method can be performed.

Here, the measurement data obtained in the atomic absorption measurement period T21 is measurement data H influenced by atomic absorption (AA) and background absorption (BG(Z)). In contrast, the measurement data obtained in the second background measurement period T23 can be considered to be equivalent to measurement data Z influenced only by background absorption (BG(Z)). Absorbance can be obtained by using the following formula (2), according to the measurement data H and Z, and measurement data Δ obtained in the dark period T22. Note that F(X) is a function representing a calculation formula for absorbance calculation on measurement data X.

Figure 4:
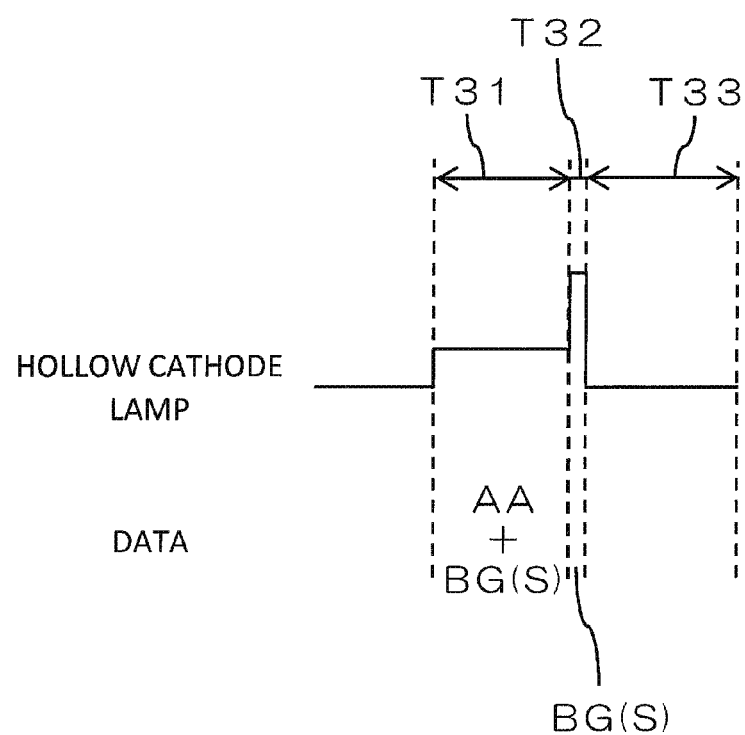
FIG. 4 is a timing chart for explaining a manner of performing background correction by using a self-reversal method.

Absorbance=$F(H-\Delta)-F(Z-\Delta)$   Formula (2):

FIG. 4 is a timing chart for explaining a manner of performing background correction by using the self-reversal method. In a case where background correction is performed by using the self-reversal method, operation of the hollow cathode lamp 1a is controlled in a predetermined manner, and thus the measurement data acquisition processing unit 100 acquires signals output from the photomultiplier tube 5 as measurement data in a fixed data acquisition cycle.

The above data acquisition cycle in background correction performed by using the self-reversal method includes an atomic absorption measurement period T31 in which a measuring beam is emitted from the hollow cathode lamp 1a in a state where no magnetic field is generated by the magnetic field generation unit 3, a third background measurement period T32 in which a measuring beam is emitted from the hollow cathode lamp 1*a* with an overcurrent in a state where no magnetic field is generated by the magnetic field generation unit 3, and a dark period T33 provided after the third background measurement period T32. In the dark period T33, the hollow cathode lamp 1*a* is brought into an unlit state or a low-output lit state. By performing calculation according to measurement data obtained in each of the periods T31 to T33, background correction using the self-reversal method can be performed.

Here, the measurement data obtained in the atomic absorption measurement period T31 is measurement data H influenced by atomic absorption (AA) and background absorption (BG(S)). In contrast, the measurement data obtained in the third background measurement period T32 can be considered to be equivalent to measurement data S influenced only by background absorption (BG(S)). Absorbance can be obtained by the following formula (3) according to the measurement data H and S, and measurement data Δ obtained in the dark period T33. Note that F(X) is a function representing a calculation formula for absorbance calculation on measurement data X.

$$\text{Absorbance} = F(H-\Delta) - F(S-\Delta) \quad \text{Formula (3):}$$

Figure 5:
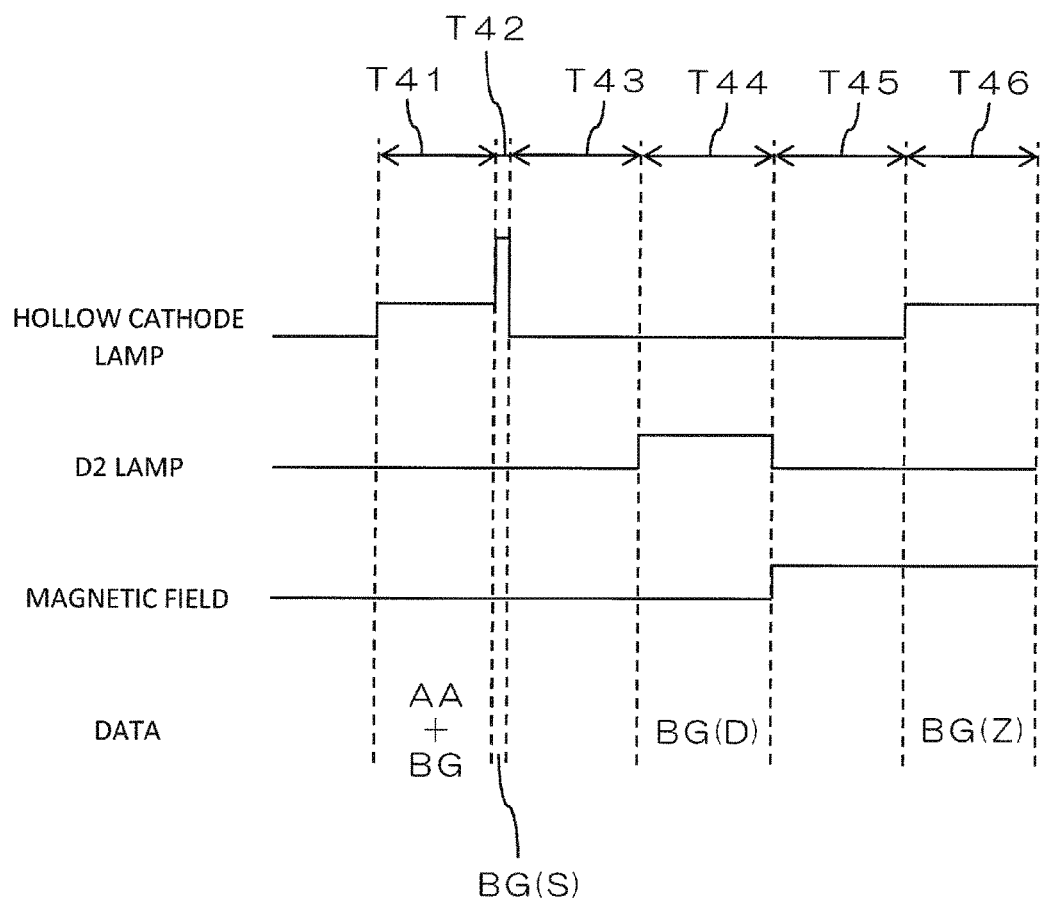
FIG. 5 is a timing chart for explaining a manner of performing background correction using the D2 lamp method, background correction using the Zeeman method, and background correction using the self-reversal method at a time.

FIG. 5 is a timing chart for explaining a manner of performing background correction by using the D2 lamp method, background correction by using the Zeeman method, and background correction by using the self-reversal method at a time. In the present embodiment, by controlling operation of the hollow cathode lamp 1*a*, operation of the deuterium lamp 1*b*, and operation of the magnetic field generation unit 3 in a predetermined manner, background correction using the D2 lamp method, background correction using the Zeeman method, and background correction using the self-reversal method can be performed at a time. At that time, the measurement data acquisition processing unit 100 acquires signals output from the photomultiplier tube 5 as measurement data in a fixed data acquisition cycle (measurement data acquisition step). The measurement data acquisition step may be performed only in a case where an operator selects a specific mode by using the operation unit 12 or may be performed every time a sample is measured.

The above data acquisition cycle in a case where background correction using the D2 lamp method, background correction using the Zeeman method, and background correction using the self-reversal method are performed at a time includes an atomic absorption measurement period T41 in which a measuring beam is emitted from the hollow cathode lamp 1*a* in a state where no magnetic field is generated by the magnetic field generation unit 3, a first background measurement period T44 in which a measuring beam is emitted from the deuterium lamp 1*b* in a state where no magnetic field is generated by the magnetic field generation unit 3, a second background measurement period T46 in which a measuring beam is emitted from the hollow cathode lamp 1*a* in a state where a magnetic field is generated by the magnetic field generation unit 3, a third background measurement period T42 in which a measuring beam is emitted from the hollow cathode lamp 1*a* with an overcurrent in a state where no magnetic field is generated by the magnetic field generation unit 3, and dark periods T43 and T45 appropriately provided between the above measurement periods. In the dark periods T43 and T45, the hollow cathode lamp 1*a* and the deuterium lamp 1*b* are brought into an unlit state or a low-output lit state. By performing calculation according to measurement data obtained in each of the periods T41 to T46, background correction using the D2 lamp method, background correction using the Zeeman method, and background correction using the self-reversal method can be performed.

Here, the measurement data obtained in the atomic absorption measurement period T41 is measurement data H influenced by atomic absorption (AA) and background absorption (BG). The measurement data obtained in the first background measurement period T44 can be considered to be equivalent to measurement data D influenced only by background absorption (BG(D)). The measurement data obtained in the second background measurement period T46 can be considered to be equivalent to measurement data Z influenced only by background absorption (BG(Z)). The measurement data obtained in the third background measurement period T42 can be considered to be equivalent to measurement data S influenced only by background absorption (BG(S)). Calculation of absorbance can be performed by using background correction using each method according to the measurement data H, D, Z and S and measurement data Δ obtained in the dark period T43 or T45.

Background correction using the D2 lamp method is performed by the first background correction processing unit 101 performing calculation according to the measurement data H obtained in the atomic absorption measurement period T41 and the measurement data D obtained in the first background measurement period T44 (first background correction step). That is, the first background correction processing unit 101 corrects the measurement data H obtained in the atomic absorption measurement period T41 by using the above formula (1), according to the measurement data D obtained in the first background measurement period T44, and calculates absorbance.

Background correction using the Zeeman method is performed by the second background correction processing unit 102 performing calculation according to the measurement data H obtained in the atomic absorption measurement period T41 and the measurement data Z obtained in the second background measurement period T46 (second background correction step). That is, the second background correction processing unit 102 corrects the measurement data H obtained in the atomic absorption measurement period T41 by using the above formula (2) according to the measurement data Z obtained in the second background measurement period T46, and calculates absorbance.

Background correction using the self-reversal method is performed by the third background correction processing unit 103 performing calculation according to the measurement data H obtained in the atomic absorption measurement period T41 and the measurement data S obtained in the third background measurement period T42 (third background correction step). That is, the third background correction processing unit 103 corrects the measurement data H obtained in the atomic absorption measurement period T41 by using the above formula (3) according to the measurement data S obtained in the third background measurement period T42, and calculates absorbance.

As described, in the present embodiment, background correction is performed by using each of the D2 lamp method, the Zeeman method, and the self-reversal method, according to measurement data in each of the measurement periods T41 to T46 obtained in one data acquisition cycle. That is, background correction is performed on the common measurement data H (atomic absorption data) obtained in the atomic absorption measurement period T41 by using each of the measurement data D, Z, and S (background data)

obtained in the first to third background measurement periods T44, T46, and T42, respectively.

Thus, background correction can be more easily performed in a shorter time period by using a plurality of types of methods while suppressing the amount of samples consumed than in a configuration where atomic absorption data and background data are obtained in each of the plurality of types of methods as described in FIGS. 2 to 4. Measurement results of background correction performed by using the respective methods are displayed on the display unit 13, for example. Therefore, an operator can easily select an optimal method even after measurement, by comparing and examining the measurement results displayed on the display unit 13.

Second Embodiment

Figure 6:
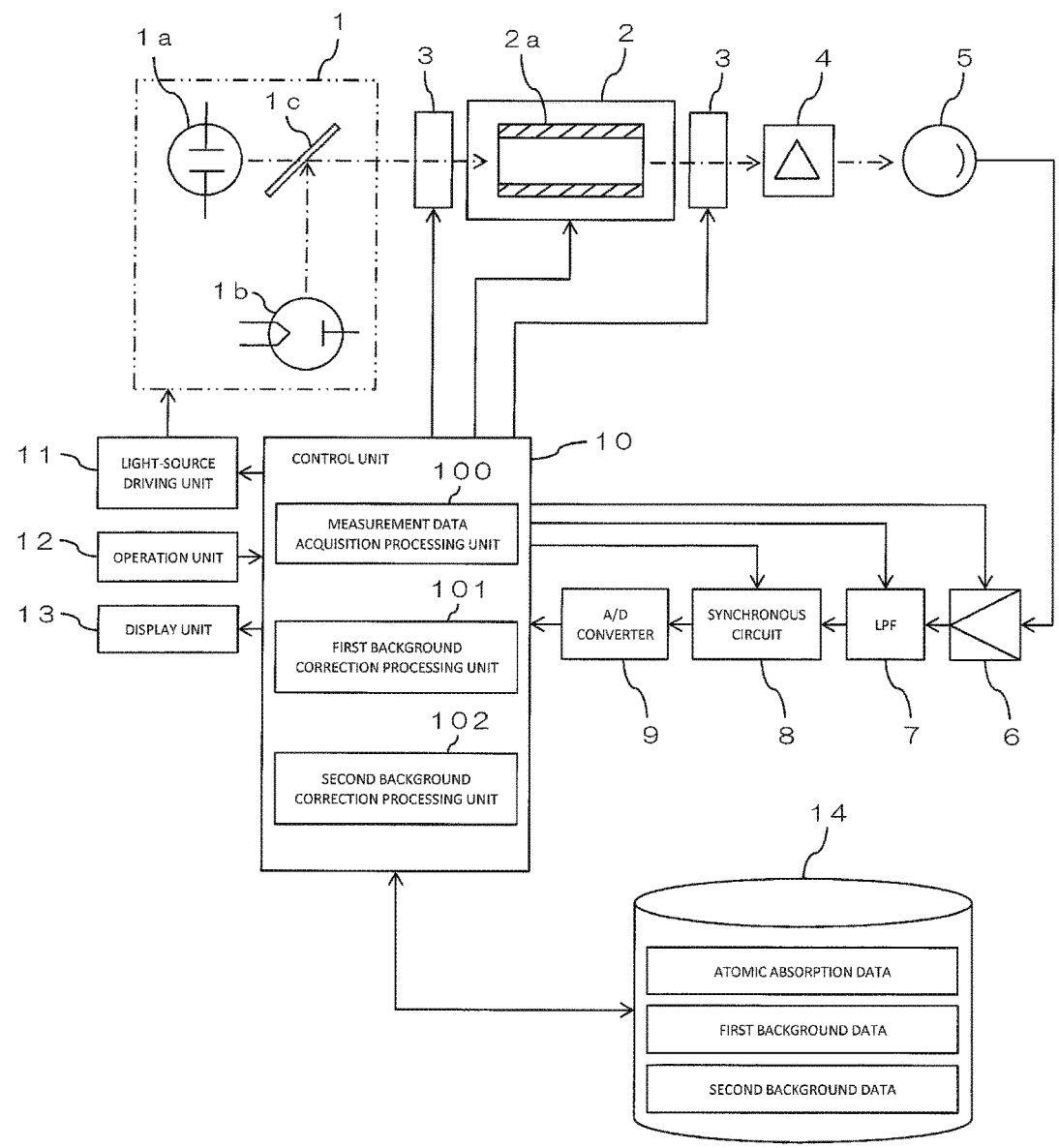
FIG. 6 is a diagram illustrating a configuration example of an atomic absorption photometer according to a second embodiment of the present invention.
Figure 7:
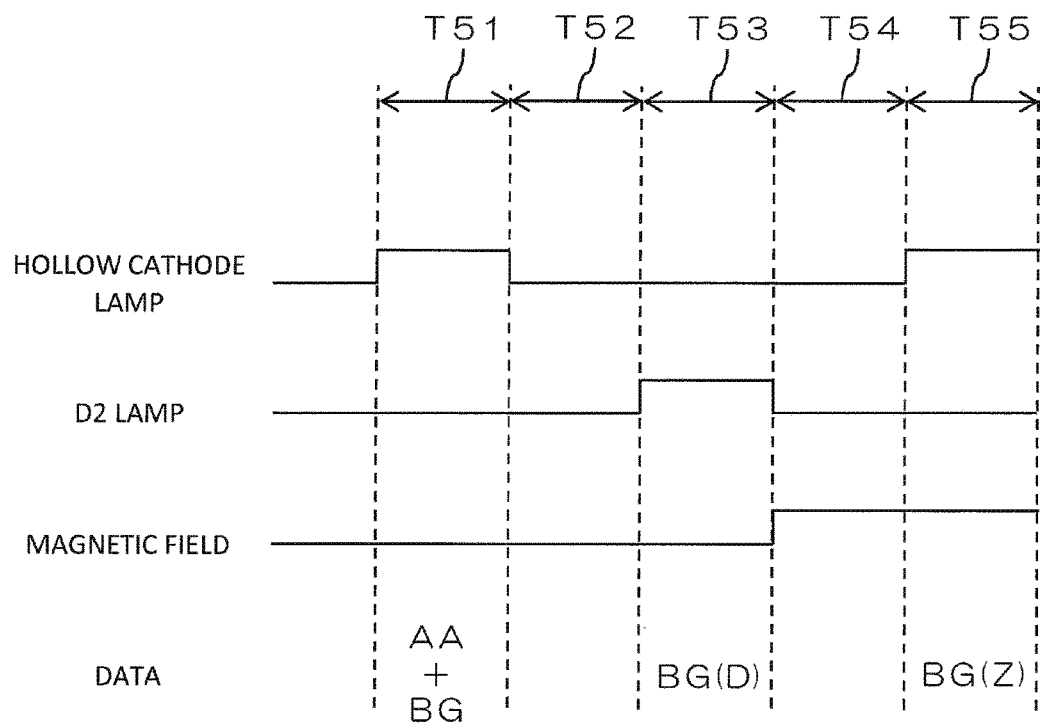
FIG. 7 is a timing chart for explaining a manner of background correction in the second embodiment.

FIG. 6 is a diagram illustrating a configuration example of an atomic absorption photometer according to a second embodiment of the present invention. FIG. 7 is a timing chart for explaining a manner of background correction in the second embodiment. The present embodiment differs from the first embodiment in that background correction using a self-reversal method is not performed and only background correction using the D2 lamp method and background correction using the Zeeman method are performed. Therefore, a control unit 10 functions as a measurement data acquisition processing unit 100, a first background correction processing unit 101, and a second background correction processing unit 102, but does not function as a third background correction processing unit 103.

That is, in the present embodiment, by controlling operation of a hollow cathode lamp 1a, operation of a deuterium lamp 1b, and operation of a magnetic field generation unit 3 in a predetermined manner, background correction using the D2 lamp method and background correction using the Zeeman method can be performed at a time. At that time, the measurement data acquisition processing unit 100 acquires signals output from a photomultiplier tube 5 as measurement data in a fixed data acquisition cycle (measurement data acquisition step). The measurement data acquisition step may be performed only in a case where an operator selects a specific mode by using an operation unit 12 or may be performed every time a sample is measured.

The above data acquisition cycle in a case where background correction using the D2 lamp method and background correction using the Zeeman method are performed at a time includes an atomic absorption measurement period T51 in which a measuring beam is emitted from the hollow cathode lamp 1a in a state where no magnetic field is generated by the magnetic field generation unit 3, a first background measurement period T53 in which a measuring beam is emitted from the deuterium lamp 1b in a state where no magnetic field is generated by the magnetic field generation unit 3, a second background measurement period T55 in which a measuring beam is emitted from the hollow cathode lamp 1a in a state where a magnetic field is generated by the magnetic field generation unit 3, and dark periods T52 and T54 appropriately provided between the above measurement periods. In the dark periods T52 and T54, the hollow cathode lamp 1a and the deuterium lamp 1b are brought into an unlit state or a low-output lit state. By performing calculation according to measurement data obtained in each of the periods T51 to T55, background correction using the D2 lamp method and background correction using the Zeeman method can be performed.

Here, the measurement data obtained in the atomic absorption measurement period T51 is measurement data H influenced by atomic absorption (AA) and background absorption (BG). The measurement data obtained in the first background measurement period T53 can be considered to be equivalent to measurement data D influenced only by background absorption (BG(D)). The measurement data obtained in the second background measurement period T55 can be considered to be equivalent to measurement data Z influenced only by background absorption (BG(Z)). Calculation of absorbance can be performed by using background correction using each method according to the measurement data H, D, and Z and measurement data Δ obtained in the dark period T52 or T54.

Background correction using the D2 lamp method is performed by the first background correction processing unit 101 performing calculation according to the measurement data H obtained in the atomic absorption measurement period T51 and the measurement data D obtained in the first background measurement period T53 (first background correction step). That is, the first background correction processing unit 101 corrects the measurement data H obtained in the atomic absorption measurement period T51 by using the above formula (1), according to the measurement data D obtained in the first background measurement period T53, and calculates absorbance.

Background correction using the Zeeman method is performed by the second background correction processing unit 102 performing calculation according to the measurement data H obtained in the atomic absorption measurement period T51 and the measurement data Z obtained in the second background measurement period T55 (second background correction step). That is, the second background correction processing unit 102 corrects the measurement data H obtained in the atomic absorption measurement period T51 by using the above formula (2), according to the measurement data Z obtained in the second background measurement period T55, and calculates absorbance.

As described, in the present embodiment, background correction is performed by using each of the D2 lamp method and the Zeeman method according to measurement data in each of the measurement periods T51 to T55 obtained in one data acquisition cycle. That is, background correction is performed on the common measurement data H (atomic absorption data) obtained in the atomic absorption measurement period T51 by using each of the measurement data D and Z (background data) obtained in the first and second background measurement periods T53 and T55, respectively.

Thus, background correction can be more easily performed in a shorter time period by using a plurality of types of methods while suppressing the amount of samples consumed than in a configuration where atomic absorption data and background data are obtained in each of the plurality of types of methods as described in FIGS. 2 and 3. Therefore, an operator can easily select an optimal method even after measurement, by comparing and examining the measurement results displayed on a display unit 13.

Third Embodiment

Figure 8:
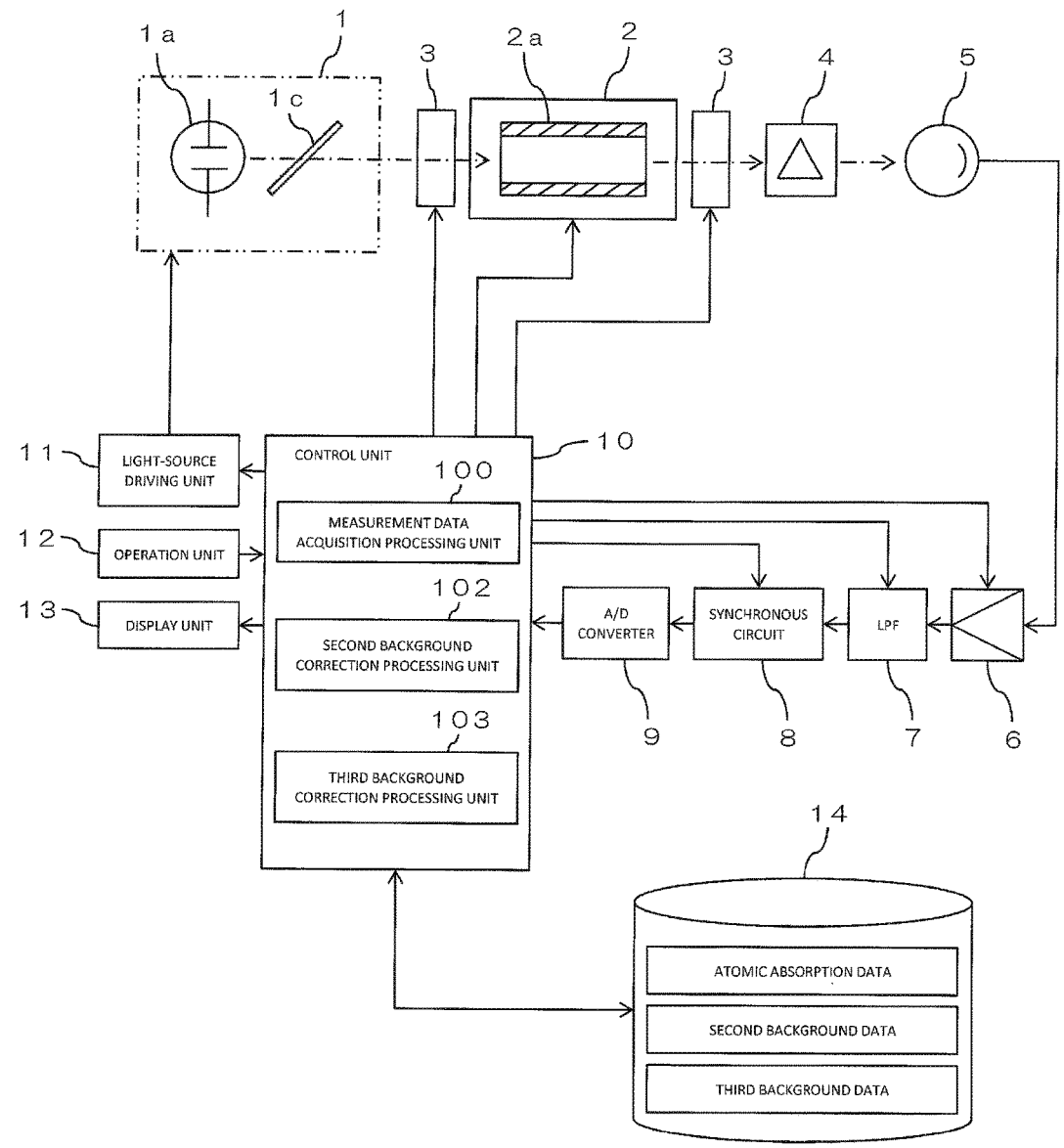
FIG. 8 is a diagram illustrating a configuration example of an atomic absorption photometer according to a third embodiment of the present invention.
Figure 9:
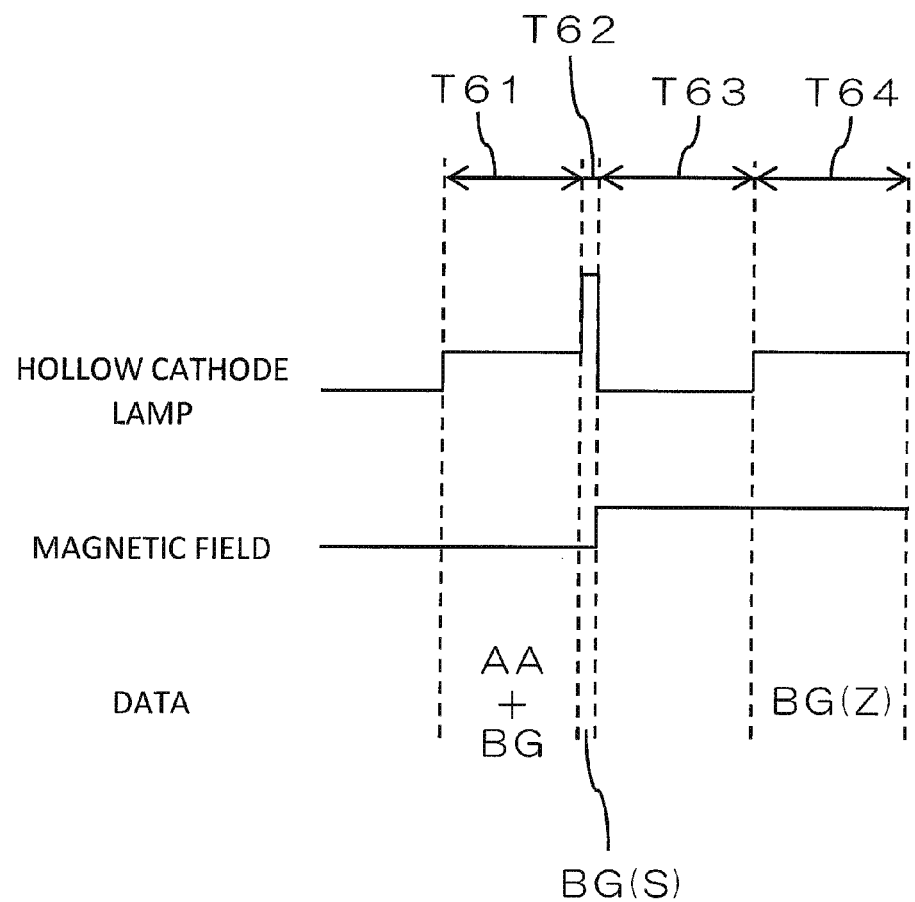
FIG. 9 is a timing chart for explaining a manner of background correction in the third embodiment.

FIG. 8 is a diagram illustrating a configuration example of an atomic absorption photometer according to a third embodiment of the present invention. FIG. 9 is a timing chart for explaining a manner of background correction in the third embodiment. The present embodiment differs from the first embodiment in that background correction using the D2 lamp method is not performed and only background correction using the Zeeman method and background correction using the self-reversal method are performed. Therefore, the atomic absorption photometer according to the present embodiment does not include a deuterium lamp 1*b*. In addition, a control unit 10 functions as a measurement data acquisition processing unit 100, a second background correction processing unit 102 and a third background correction processing unit 103, but does not function as a first background correction processing unit 101.

That is, in the present embodiment, by controlling operation of a hollow cathode lamp 1*a* and operation of a magnetic field generation unit 3 in a predetermined manner, background correction using the Zeeman method and background correction using the self-reversal method can be performed at a time. At that time, the measurement data acquisition processing unit 100 acquires signals output from a photomultiplier tube 5 as measurement data in a fixed data acquisition cycle (measurement data acquisition step). The measurement data acquisition step may be performed only in a case where an operator selects a specific mode by using an operation unit 12 or may be performed every time a sample is measured.

The above data acquisition cycle in a case where background correction using the Zeeman method and background correction using the self-reversal method are performed at a time includes an atomic absorption measurement period T61 in which a measuring beam is emitted from the hollow cathode lamp 1*a* in a state where no magnetic field is generated by the magnetic field generation unit 3, a second background measurement period T64 in which a measuring beam is emitted from the hollow cathode lamp 1*a* in a state where a magnetic field is generated by the magnetic field generation unit 3, a third background measurement period T62 in which a measuring beam is emitted from the hollow cathode lamp 1*a* with an overcurrent in a state where no magnetic field is generated by the magnetic field generation unit 3, and a dark period T63 appropriately provided between the above measurement periods. In the dark period T63, the hollow cathode lamp 1*a* is brought into an unlit state or a low-output lit state. By performing calculation according to measurement data obtained in each of the periods T61 to T64, background correction using the Zeeman method and background correction using the self-reversal method can be performed.

Here, the measurement data obtained in the atomic absorption measurement period T61 is measurement data H influenced by atomic absorption (AA) and background absorption (BG). The measurement data obtained in the second background measurement period T64 can be considered to be equivalent to measurement data Z influenced only by background absorption (BG(Z)). The measurement data obtained in the third background measurement period T62 can be considered to be equivalent to measurement data S influenced only by background absorption (BG(S)). Calculation of absorbance can be performed by using background correction using each method according to the measurement data H, Z, and S and measurement data Δ obtained in the dark period T63.

Background correction using the Zeeman method is performed by the second background correction processing unit 102 performing calculation according to the measurement data H obtained in the atomic absorption measurement period T61 and the measurement data Z obtained in the second background measurement period T64 (second background correction step). That is, the second background correction processing unit 102 corrects the measurement data H obtained in the atomic absorption measurement period T61 by using the above formula (2) according to the measurement data Z obtained in the second background measurement period T64, and calculates absorbance.

Background correction using the self-reversal method is performed by the third background correction processing unit 103 performing calculation according to the measurement data H obtained in the atomic absorption measurement period T61 and the measurement data S obtained in the third background measurement period T62 (third background correction step). That is, the third background correction processing unit 103 corrects the measurement data H obtained in the atomic absorption measurement period T61 by using the above formula (3) according to the measurement data S obtained in the third background measurement period T62, and calculates absorbance.

As described, in the present embodiment, background correction is performed by using each of the Zeeman method and the self-reversal method according to measurement data in each of the measurement periods T61 to T64 obtained in one data acquisition cycle. That is, background correction is performed on the common measurement data H (atomic absorption data) obtained in the atomic absorption measurement period T61 by using each of the measurement data Z and S (background data) obtained in the second and third background measurement periods T64 and T62, respectively.

Thus, background correction can be more easily performed in a shorter time period by using a plurality of types of methods while suppressing the amount of samples consumed than in a configuration where atomic absorption data and background data are obtained for each of the plurality of types of methods as described in FIGS. 3 and 4. Therefore, an operator can easily select an optimal method even after measurement, by comparing and examining the measurement results displayed on a display unit 13.

Fourth Embodiment

Figure 10:
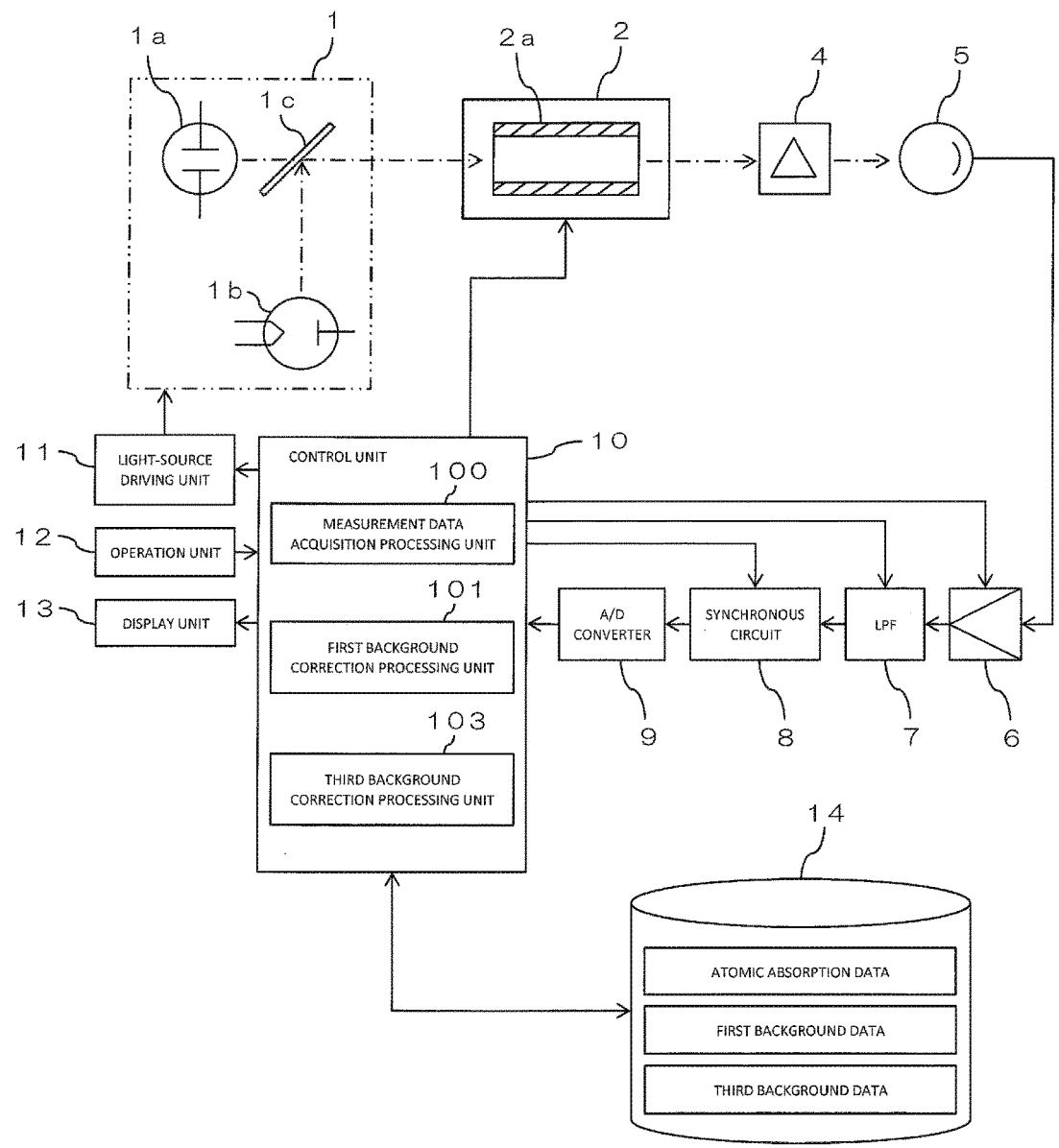
FIG. 10 is a diagram illustrating a configuration example of an atomic absorption photometer according to a fourth embodiment of the present invention.
Figure 11:
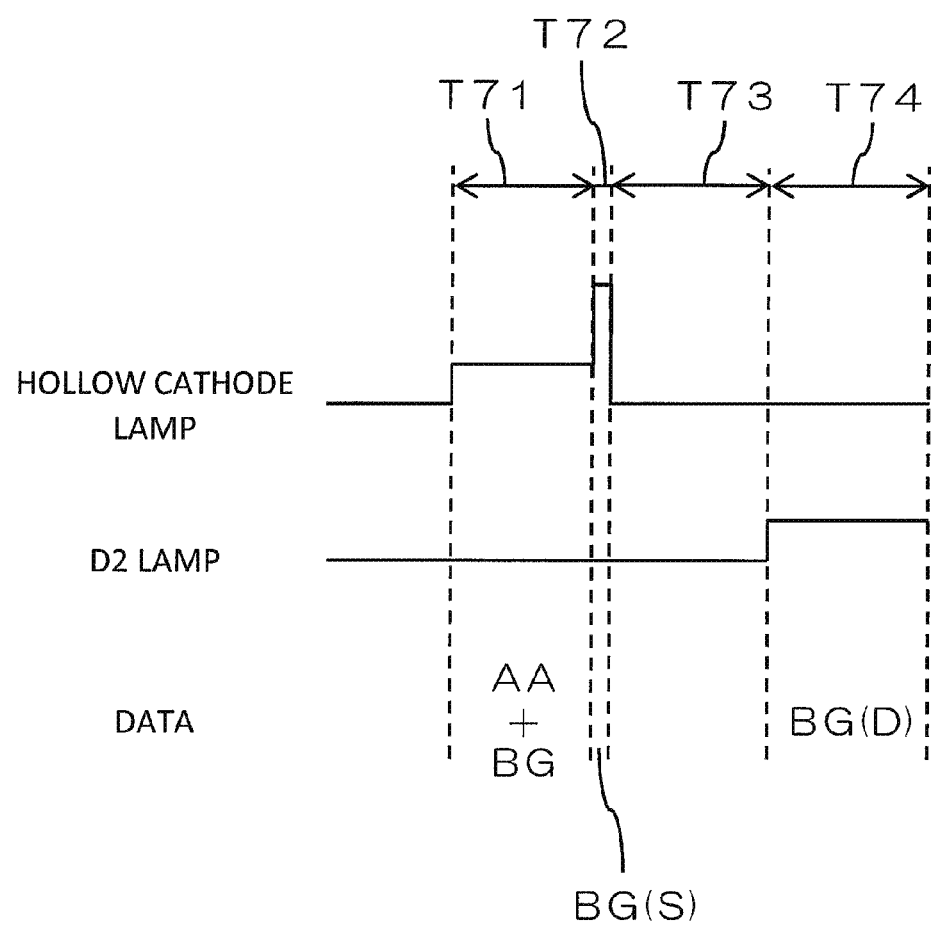
FIG. 11 is a timing chart for explaining a manner of background correction in the fourth embodiment.

FIG. 10 is a diagram illustrating a configuration example of an atomic absorption photometer according to a fourth embodiment of the present invention. FIG. 11 is a timing chart for explaining a manner of background correction in the fourth embodiment. The present embodiment differs from the first embodiment in that background correction using the Zeeman method is not performed and only background correction using the D2 lamp method and background correction using the self-reversal method are performed. Therefore, the atomic absorption photometer according to the present embodiment does not include a magnetic field generation unit 3. In addition, a control unit 10 functions as a measurement data acquisition processing unit 100, a first background correction processing unit 101 and a third background correction processing unit 103, but does not function as a second background correction processing unit 102.

That is, in the present embodiment, by controlling operation of a hollow cathode lamp 1*a* and operation of a deuterium lamp 1*b* in a predetermined manner, background correction using the D2 lamp method and background correction using the self-reversal method can be performed at a time. At that time, the measurement data acquisition processing unit 100 acquires signals output from a photomultiplier tube 5 as measurement data in a fixed data acquisition cycle (measurement data acquisition step). The measurement data acquisition step may be performed only in a case where an operator selects a specific mode by using an operation unit 12 or may be performed every time a sample is measured.

The above data acquisition cycle in a case where background correction using the D2 lamp method and background correction using the self-reversal method are performed at a time includes an atomic absorption measurement period T71 in which a measuring beam is emitted from the hollow cathode lamp 1a, a first background measurement period T74 in which a measuring beam is emitted from the deuterium lamp 1b, a third background measurement period T72 in which a measuring beam is emitted from the hollow cathode lamp 1a with an overcurrent, and a dark period T73 appropriately provided between the above measurement periods. In the dark period T73, the hollow cathode lamp 1a and the deuterium lamp 1b are brought into an unlit state or a low-output lit state. By performing calculation according to measurement data obtained in each of the periods T71 to T74, background correction using the D2 lamp method and background correction using the self-reversal method can be performed.

Here, the measurement data obtained in the atomic absorption measurement period T71 is measurement data H influenced by atomic absorption (AA) and background absorption (BG). The measurement data obtained in the first background measurement period T74 can be considered to be equivalent to measurement data D influenced only by background absorption (BG(D)). The measurement data obtained in the third background measurement period T72 can be considered to be equivalent to measurement data S influenced only by background absorption (BG(S)). Calculation of absorbance can be performed by using background correction using each method, according to the measurement data H, D, and S and measurement data Δ obtained in the dark period T73.

Background correction using the D2 lamp method is performed by the first background correction processing unit 101 performing calculation according to the measurement data H obtained in the atomic absorption measurement period T71 and the measurement data D obtained in the first background measurement period T74 (first background correction step). That is, the first background correction processing unit 101 corrects the measurement data H obtained in the atomic absorption measurement period T71 by using the above formula (1) according to the measurement data D obtained in the first background measurement period T74, and calculates absorbance.

Background correction using the self-reversal method is performed by the third background correction processing unit 103 performing calculation according to the measurement data H obtained in the atomic absorption measurement period T71 and the measurement data S obtained in the third background measurement period T72 (third background correction step). That is, the third background correction processing unit 103 corrects the measurement data H obtained in the atomic absorption measurement period T71 by using the above formula (3) according to the measurement data S obtained in the third background measurement period T72, and calculates absorbance.

As described, in the present embodiment, background correction is performed by using each of the D2 lamp method and the self-reversal method according to measurement data in each of the measurement periods T71 to T74 obtained in one data acquisition cycle. That is, background correction is performed on the common measurement data H (atomic absorption data) obtained in the atomic absorption measurement period T71 by using each of the measurement data D and S (background data) obtained in the first and third background measurement periods T74 and T72, respectively.

Thus, background correction can be more easily performed in a shorter time period by using a plurality of types of methods while suppressing the amount of samples consumed than in a configuration where atomic absorption data and background data are obtained in each of the plurality of types of methods as described in FIGS. 2 and 4. Therefore, an operator can easily select an optimal method even after measurement, by comparing and examining the measurement results displayed on a display unit 13.

In the above embodiments, the configurations have been described where background correction is performed by using not only measurement data obtained in the atomic absorption measurement period and the background measurement periods, but also measurement data obtained in the dark period. However, the present invention is not limited to such a configuration and may have a configuration where background correction is performed without using measurement data obtained in the dark period.

The first light source which emits a measuring beam for atomic absorption measurement is not limited to be the hollow cathode lamp 1a and may be another light source which emits a measuring beam including a bright line spectrum. In addition, a light source which emits a measuring beam including a continuous spectrum, such as a xenon flash lamp, may also be used as the first light source.

In the above embodiments, the configurations have been described where the present invention is applied to the furnace-type atomic absorption photometer. However, the present invention is not limited to the furnace-type atomic absorption photometer and can be applied to, for example, a frame-type atomic absorption photometer in which a sample is sprayed to a combustible gas, the sample is heated and atomized by burning the obtained mixed gas, a measuring beam is passed through generated atomic vapor, and absorbance of the sample is measured.

DESCRIPTION OF REFERENCE SIGNS

1 light source unit
1a hollow cathode lamp
1b deuterium lamp
1c half mirror
2 atomization unit
2a graphite tube
3 magnetic field generation unit
4 spectroscope
5 photomultiplier tube
6 amplifier
7 low-pass filter (LPF)
8 synchronous circuit
9 A/D converter
10 control unit
11 light-source driving unit
12 operation unit
13 display unit
14 memory
100 measurement data acquisition processing unit
101 first background correction processing unit
102 second background correction processing unit
103 third background correction processing unit

The invention claimed is:
1. An atomic absorption photometer comprising:
an atomizer configured to generate atomic vapor by atomizing a sample;

a first light source configured to irradiate the atomic vapor generated at the atomizer with a measuring beam for atomic absorption measurement;
a second light source configured to irradiate the atomic vapor generated at the atomizer with a measuring beam for background measurement;
a magnetic field generator configured to generate a magnetic field at the atomizer;
a detector configured to acquire measurement data by detecting light having passed through the atomizer; and
a processor configured to:
   acquire measurement data in each of an atomic absorption measurement period in which a measuring beam is emitted from the first light source in a state where no magnetic field is generated by the magnetic field generator, a first background measurement period in which a measuring beam is emitted from the second light source in a state where no magnetic field is generated by the magnetic field generator, a second background measurement period in which a measuring beam is emitted from the first light source in a state where a magnetic field is generated by the magnetic field generator, and a third background measurement period in which a measuring beam is emitted from the first light source with an overcurrent in a state where no magnetic field is generated by the magnetic field generator, in a single data acquisition cycle including the atomic absorption measurement period, the first background measurement period, the second background measurement period, and the third background measurement period;
   correct the measurement data obtained in the atomic absorption measurement period by using a D2 lamp method, according to the measurement data obtained in the first background measurement period;
   correct the measurement data obtained in the atomic absorption measurement period by using a Zeeman method, according to the measurement data obtained in the second background measurement period; and
   correct the measurement data obtained in the atomic absorption measurement period by using a self-reversal method, according to the measurement data obtained in the third background measurement period.

2. An atomic absorption photometer comprising:
an atomizer configured to generate atomic vapor by atomizing a sample;
a first light source configured to irradiate the atomic vapor generated at the atomizer with a measuring beam for atomic absorption measurement;
a second light source configured to irradiate the atomic vapor generated at the atomizer with a measuring beam for background measurement;
a magnetic field generator configured to generate a magnetic field at the atomizer;
a detector configured to acquire measurement data by detecting light having passed through the atomizer; and
a processor configured to:
   acquire measurement data in each of an atomic absorption measurement period in which a measuring beam is emitted from the first light source in a state where no magnetic field is generated by the magnetic field generator, a first background measurement period in which a measuring beam is emitted from the second light source in a state where no magnetic field is generated by the magnetic field generator, and a second background measurement period in which a measuring beam is emitted from the first light source in a state where a magnetic field is generated by the magnetic field generator, in a single data acquisition cycle including the atomic absorption measurement period, the first background measurement period, and the second background measurement period;
   correct the measurement data obtained in the atomic absorption measurement period by using a D2 lamp method, according to the measurement data obtained in the first background measurement period; and
   correct the measurement data obtained in the atomic absorption measurement period by using a Zeeman method, according to the measurement data obtained in the second background measurement period.

3. An atomic absorption photometer comprising:
an atomizer configured to generate atomic vapor by atomizing a sample;
a first light source configured to irradiate the atomic vapor generated at the atomizer with a measuring beam for atomic absorption measurement;
a magnetic field generator configured to generate a magnetic field at the atomizer;
a detector configured to acquire measurement data by detecting light having passed through the atomizer; and
a processor configured to:
   acquire measurement data in each of an atomic absorption measurement period in which a measuring beam is emitted from the first light source in a state where no magnetic field is generated by the magnetic field generator, a second background measurement period in which a measuring beam is emitted from the first light source in a state where a magnetic field is generated by the magnetic field generator, and a third background measurement period in which a measuring beam is emitted from the first light source with an overcurrent in a state where no magnetic field is generated by the magnetic field generator, in a single data acquisition cycle including the atomic absorption measurement period, the second background measurement period, and the third background measurement period;
   correct the measurement data obtained in the atomic absorption measurement period by using a Zeeman method, according to the measurement data obtained in the second background measurement period; and
   correct the measurement data obtained in the atomic absorption measurement period by using a self-reversal method, according to the measurement data obtained in the third background measurement period.

4. An atomic absorption measurement method for measuring atomic absorption by using an atomic absorption photometer including: an atomizer configured to generate atomic vapor by atomizing a sample; a first light source configured to irradiate the atomic vapor generated at the atomizer with a measuring beam for atomic absorption measurement; a second light source configured to irradiate the atomic vapor generated at the atomizer with a measuring beam for background measurement; a magnetic field generator configured to generate a magnetic field at the atomizer; and a detector configured to acquire measurement data by detecting light having passed through the atomizer, the method comprising:
a measurement data acquisition step of acquiring measurement data in each of an atomic absorption measurement period in which a measuring beam is emitted from the first light source in a state where no magnetic field is generated by the magnetic field generator, a first background measurement period in which a measuring beam is emitted from the second light source in a state where no magnetic field is generated by the magnetic field generator, a second background measurement period in which a measuring beam is emitted from the first light source in a state where a magnetic field is generated by the magnetic field generator, and a third background measurement period in which a measuring beam is emitted from the first light source with an overcurrent in a state where no magnetic field is generated by the magnetic field generator, in a single data acquisition cycle including the atomic absorption measurement period, the first background measurement period, the second background measurement period, and the third background measurement period;

a first background correction step of correcting the measurement data obtained in the atomic absorption measurement period by using a D2 lamp method, according to the measurement data obtained in the first background measurement period;

a second background correction step of correcting the measurement data obtained in the atomic absorption measurement period by using a Zeeman method, according to the measurement data obtained in the second background measurement period; and a third background correction step of correcting the measurement data obtained in the atomic absorption measurement period by using a self-reversal method, according to the measurement data obtained in the third background measurement period.

5. An atomic absorption measurement method for measuring atomic absorption by using an atomic absorption photometer including: an atomizer configured to generate atomic vapor by atomizing a sample; a first light source configured to irradiate the atomic vapor generated at the atomizer with a measuring beam for atomic absorption measurement; a second light source configured to irradiate the atomic vapor generated at the atomizer with a measuring beam for background measurement; a magnetic field generator configured to generate a magnetic field at the atomizer; and a detector configured to acquire measurement data by detecting light having passed through the atomizer, the method comprising:

a measurement data acquisition step of acquiring measurement data in each of an atomic absorption measurement period in which a measuring beam is emitted from the first light source in a state where no magnetic field is generated by the magnetic field generator, a first background measurement period in which a measuring beam is emitted from the second light source in a state where no magnetic field is generated by the magnetic field generator, and a second background measurement period in which a measuring beam is emitted from the first light source in a state where a magnetic field is generated by the magnetic field generator, in a single data acquisition cycle including the atomic absorption measurement period, the first background measurement period, and the second background measurement period, a first background correction step of correcting the measurement data obtained in the atomic absorption measurement period by using a D2 lamp method, according to the measurement data obtained in the first background measurement period; and a second background correction step of correcting the measurement data obtained in the atomic absorption measurement period by using a Zeeman method, according to the measurement data obtained in the second background measurement period.

6. An atomic absorption measurement method for measuring atomic absorption by using an atomic absorption photometer including: an atomizer configured to generate atomic vapor by atomizing a sample; a first light source configured to irradiate the atomic vapor generated at the atomizer with a measuring beam for atomic absorption measurement; a magnetic field generator configured to generate a magnetic field at the atomizer, and a detector configured to acquire measurement data by detecting light having passed through the atomizer, the method comprising:

a measurement data acquisition step of acquiring measurement data in each of an atomic absorption measurement period in which a measuring beam is emitted from the first light source in a state where no magnetic field is generated by the magnetic field generator, a second background measurement period in which a measuring beam is emitted from the first light source in a state where a magnetic field is generated by the magnetic field generator, and a third background measurement period in which a measuring beam is emitted from the first light source with an overcurrent in a state where no magnetic field is generated by the magnetic field generator, in a single data acquisition cycle including the atomic absorption measurement period, the second background measurement period, and the third background measurement period;

a second background correction step of correcting the measurement data obtained in the atomic absorption measurement period by using a Zeeman method, according to the measurement data obtained in the second background measurement period; and a third background correction step of correcting the measurement data obtained in the atomic absorption measurement period by using a self-reversal method, according to the measurement data obtained in the third background measurement period.

7. The atomic absorption photometer of claim 1, wherein the measuring beam is emitted from the second light source once during the single data acquisition cycle.

* * * * *